United States Patent [19]

Thomas et al.

[11] 4,330,627
[45] May 18, 1982

[54] TESTING TRAY

[75] Inventors: Michael D. Thomas; Francis E. Ryder, both of Arab, Ala.

[73] Assignee: Ryder International Corporation, Arab, Ala.

[21] Appl. No.: 10,954

[22] Filed: Feb. 9, 1979

[51] Int. Cl.³ ............................................. C12M 1/20
[52] U.S. Cl. ..................................... 435/301; 422/61; 435/34; 435/293; 435/808; 435/810
[58] Field of Search ...................... 422/61; 435/32, 33, 435/29, 30, 34, 38, 292, 293, 294, 299, 300, 301, 808, 810, 287

[56] References Cited

U.S. PATENT DOCUMENTS

| | | | |
|---|---|---|---|
| D. 213,032 | 12/1968 | Michel | D83/1 |
| D. 224,457 | 7/1972 | Oppenheimer | D83/1 |
| D. 241,173 | 8/1976 | Corneille | D83/1 U |
| D. 241,174 | 8/1976 | Corneille | D83/1 U |
| D. 243,542 | 3/1977 | Fadler et al. | D24/29 |
| D. 243,543 | 3/1977 | Fadler et al. | D24/29 |
| 3,799,742 | 3/1974 | Coleman | 23/253 R |
| 4,260,687 | 4/1981 | Jacobson et al. | 435/301 |

FOREIGN PATENT DOCUMENTS 1220083 6/1966 Fed. Rep. of Germany ........ 435/32

Primary Examiner—Robert J. Warden
Attorney, Agent, or Firm—Trexler, Bushnell & Wolters, Ltd.

[57] ABSTRACT

The present disclosure relates to a testing tray for use in the conducting of a series of tests on a liquid specimen such as a blood or urine sample, with the results of the individual test being used to provide means for identification of a microorganism present in said specimens. The testing tray includes a plurality of test channels, which are of a generally U-shaped or reverse bend configuration, each channel including an entry portion and a testing portion comprised of one or more test chambers. The testing portions of the respective channels are closed by a transparent plastic sheet or strip which is affixed to the base in overlying relation to the various channels. The strip is sealed to the upper surface of the base intermediate the respective channels to effectively isolate one from the other, while leaving the entry portion of each channel open for the introduction of a liquid specimen therein. A pivotally connected cover member is provided which includes a section of absorbent material, which cover member may be closed to overlie the test channel entry portions. Further, the testing tray includes desiccant means to purge the test channel of undesired moisture during storage, prior to use of the tray.

6 Claims, 6 Drawing Figures

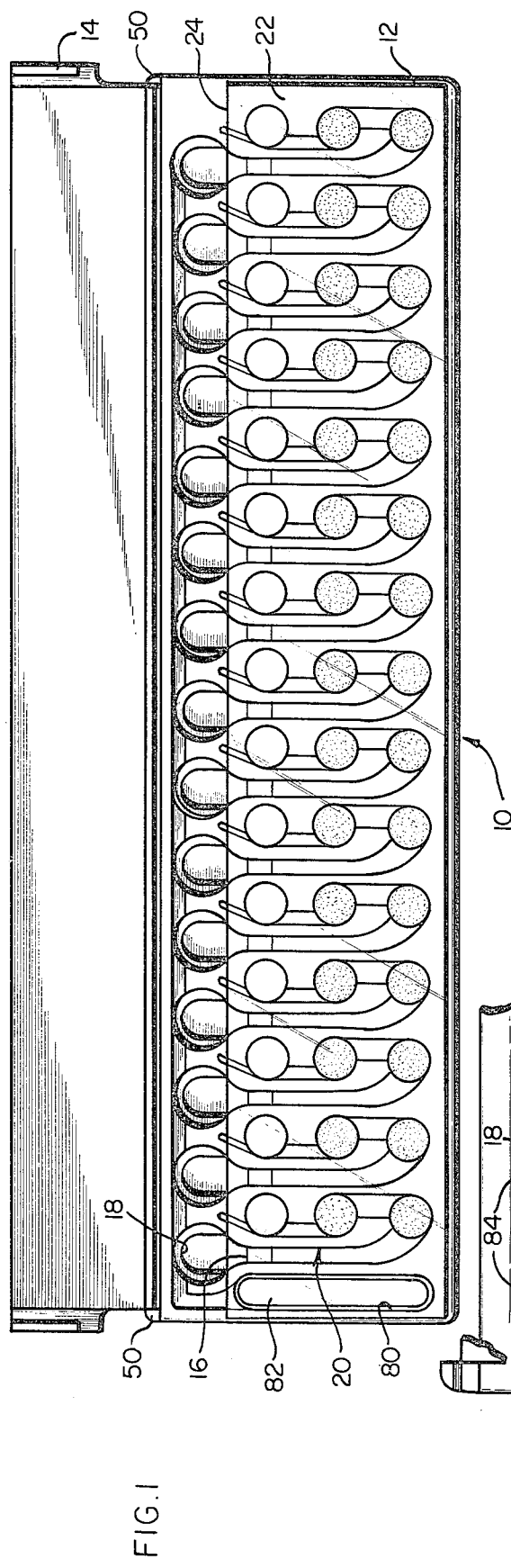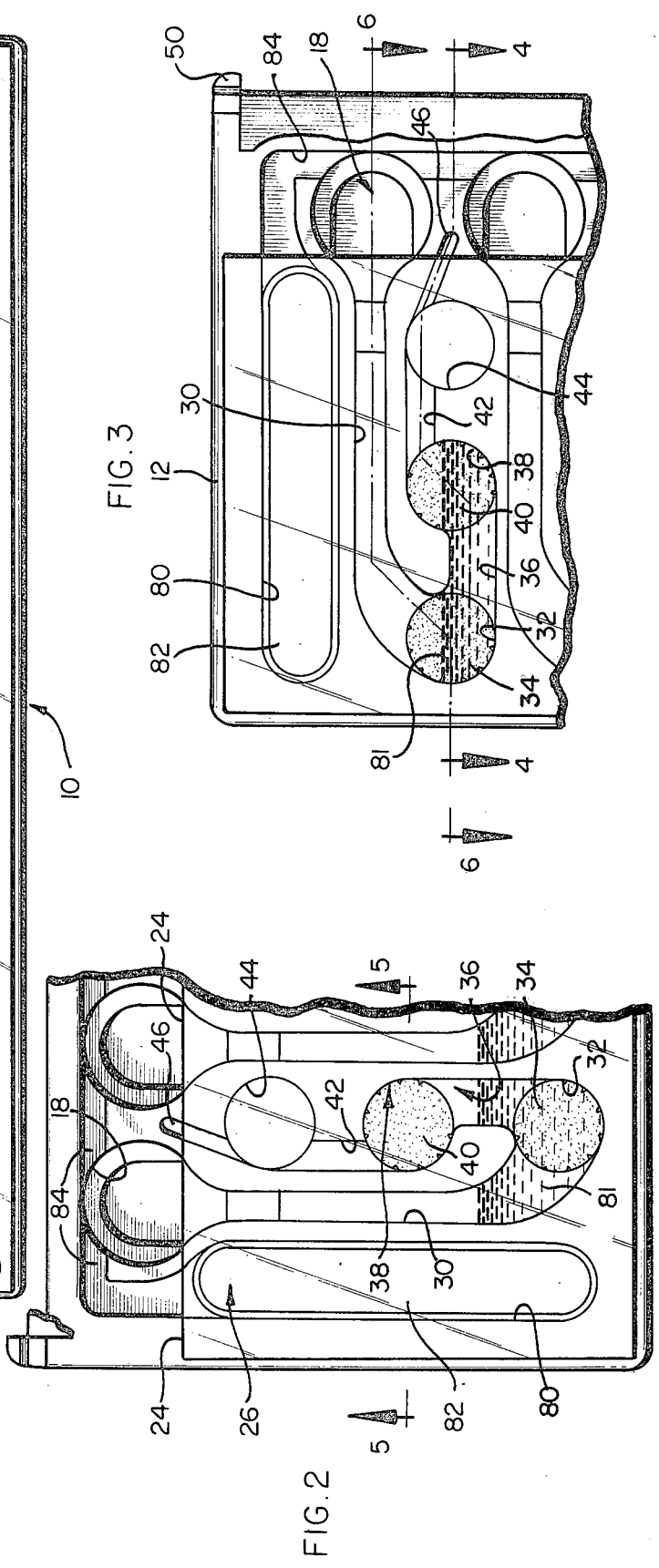
FIG. 1
FIG. 2
FIG. 3

U.S. Patent  May 18, 1982  Sheet 2 of 2  4,330,627
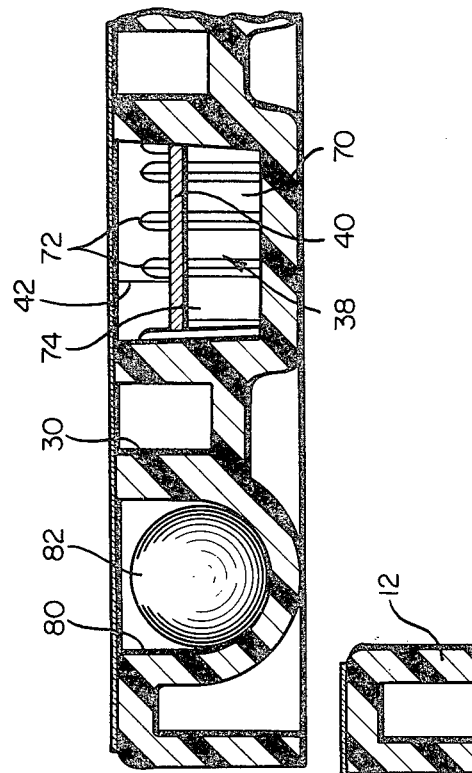
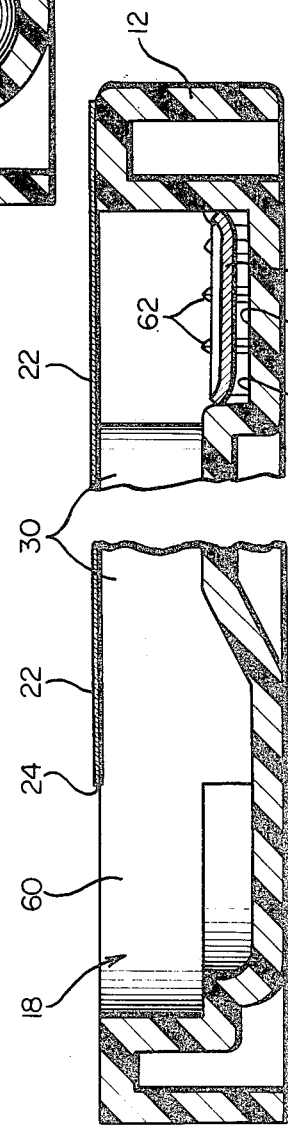
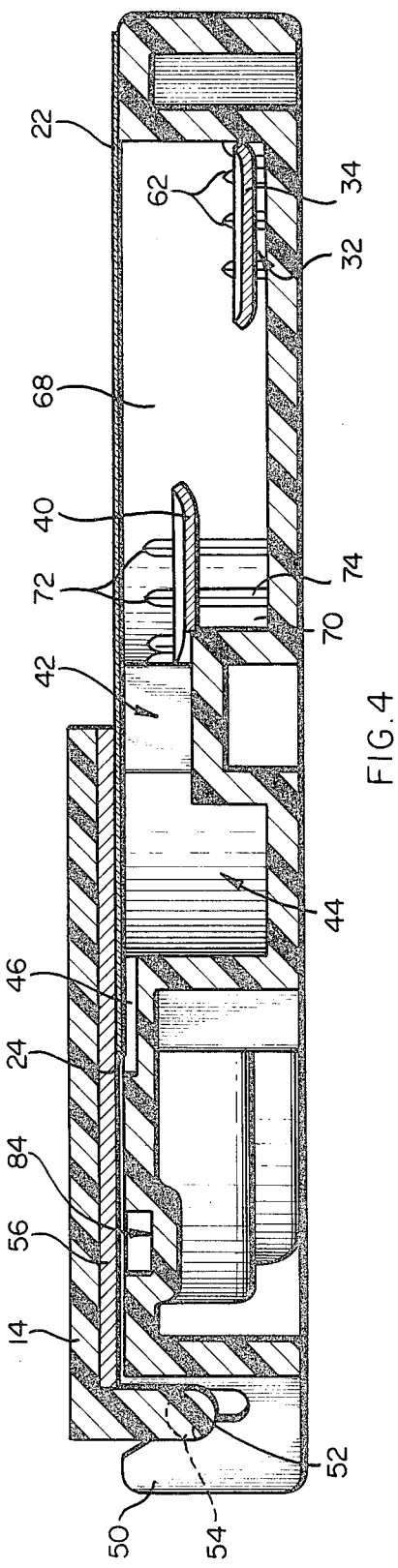

TESTING TRAY

BACKGROUND OF THE INVENTION

The present invention pertains to a testing tray, and more particularly to an improved testing tray design for the conducting of a plurality of biochemical tests on a liquid specimen such as a blood or urine sample, wherein the results of the various tests performed may be utilized to provide an identification of any microorganisms present in the sample.

In the treatment of patients suffering from an unknown disease, it is extremely important, and often critical, that the physician determine the particular microorganism or bacteria present in the patient which may be causing the disease and its associated symptoms. Microbiologists are aware of literally thousands of disease-causing microorganisms, and have sought to find reliable and convenient methods or test procedures for identification thereof. In this regard, identification of an unknown microorganism is usually achieved by the conducting of a series of known or standard biochemical tests, and then comparing the positive and negative results of these tests with known reaction patterns that have been developed and determined to be common with respect to a particular microorganism.

The various identification tests are usually performed upon a prepared liquid specimen such as a blood or urine sample, which has been incubated for a prescribed period of time so as to develop a sufficient culture of the microorganism. The tests performed involve the use of specially prepared reagent papers which may change color or not, thereby indicating a positive or negative reaction, depending upon the particular test involved and the presence or lack of presence of a microorganism in the specimen. The tests may be performed utilizing various apparatus, such as separate test tubes, or a specially designed tray. The aforementioned tray provides a plurality of separate and isolated test chambers, one for each of the tests to be performed, with a clear plastic cover overlying the test channels and chambers to permit the technician to view a segment of reagent paper or disc disposed within the test chamber. In this regard, the different reagent discs employed in the respective channels have been specially prepared, depending upon the test to be performed, will change color or not depending upon whether the test is positive or negative.

The above-discussed known types of testing trays while satisfactory in many respects are subject to certain disadvantages, which are believed overcome by the present invention, as will be discussed hereinafter and as is believed will become clear from the detailed description of the drawings which follows. By way of example, the testing trays are usually packed in a sealed envelope, and problems have been encountered in that unwanted moisutre may develop in the testing channels due to condensation. With the present invention, a desiccant means is provided which alleviates this problem. Another problem is the necessity of protecting the technician from infection by the microorganisms present in the sample. In this regard, the present invention employs a pivotally mounted cover with an absorbent portion which will overlie the entry portion to each test channel, the absorbent portion being porous, and absorbing any extraneous liquid which may have been spilled on the tray during introduction of the specimen into the test channels, or pursuant to handling of the tray thereafter. As a further matter, since certain of the tests performed may require the addition of a chemical to the test channel after injection of the liquid specimen therein, the cover member with its absorbent portion serves to prevent cross-contamination of the respective channels.

Other structural and operational features of the present invention will become apparent from the detailed description of the invention which will follow in conjunction with the hereinafter described drawings.

DESCRIPTION OF THE DRAWINGS

FIG. 1 is a front plan view of a tray in accordance with the present invention, disposed in a vertical orientation with the cover in the open position;

FIG. 2 is an enlarged, partial plan view of the tray of FIG. 1 and illustrates one of the test channels with a quantity of liquid specimen therein;

FIG. 3 is a partial view similar to that of FIG. 2, but with the tray rotated 90°, thereby introducing the liquid specimen into an additional portion of the test channel;

FIG. 4 is a sectional view taken along the section line 4—4 of FIG. 1, which section line follows the path of the test channel, as indicated;

FIG. 5 is a partial sectional view taken along the section line 5—5 of FIG. 2; and FIG. 6 is a sectional view taken along the section line 6—6 of FIG. 3, which section line follows the path of the test channel, as indicated.

DESCRIPTION OF THE ILLUSTRATED EMBODIMENT

The drawings, most particularly, FIG. 1, illustrate a testing tray for use in the performing of a series of tests on a liquid specimen or the like, which tray is designated generally 10. Before discussing in detail the process or method of utilizing the tray 10 in conjunction with the tests to be conducted, it is believed advantageous to consider first the structural features or design of the tray, and accordingly the discussion will proceed along these lines.

Basically, the tray 10 includes a base 12 to which a lid or cover member 14 is pivotally connected. Formed in the base 12, are a plurality of generally U-shaped or reverse bent, closed bottom channels 16 which are utilized to perform various tests as will be described. The various channels are of similar design, and as such only the left-most channel as viewed, will be discussed in detail. In this regard, it should be noted that each channel includes generally an entry segment 18 and a test conducting segment designated generally 20. To close the test conducting segment 20 of each test channel, there is employed a sheet of clear plastic material 22 which is affixed to the upper surface of the base 12 in overlying relation to the test segments 20 of the respective channels. In this regard, it should be noted that the sheet 20 is sealed to the upper surface of the base 12 intermediate the respective channels, and as such prevents cross-contamination of the test being conducted in the respective channels. As a further matter, the upper edge 24 of the clear plastic sheet 22 is disposed such that a portion of the entry segment 18 of each channel 16 is left uncovered for the injection therein of the liquid specimen.

Looking now to FIGS. 2-6, the construction of an individual test channel 16 will now be considered with regard to the left-most channel as viewed in FIG. 2, keeping in mind that the remaining channels 16 are of identical construction. FIG. 2 as can be seen is an enlarged view of the left-hand portion of the tray 10 of FIG. 1, and in addition to the single test channel 16 also illustrates a desiccant chamber and channel means, designated generally 26, to be discussed more fully hereinafter.

With respect to the test channel 16, it should be noted that the entry portion thereof is in the form of a generally circular well with an elongate narrow channel section 30 extending downwardly therefrom. The narrow channel section 30 communicates with a first or lower test chamber 32 the construction of which will be discussed with respect to FIG. 5. Disposed in the first or lower test chamber 32 is an initial or first reagent disc 34, which is a paper disc which has been specially treated in a known manner in relation to the particular test to be performed in the channel. The test chamber 32 defines the lower-most portion of the testing channel 16, and there is provided a second elongate narrow channel section 36 which extends upwardly from the chamber 32, and is separate from the previously mentioned channel section 30. The narrow channel section 36 opens to a second test chamber 38 in which there may be disposed a second reagent disc 40, as illustrated in FIG. 2. A third relatively narrow, channel section 42 extends upwardly from the second test channel 38 and opens to a third chamber 44, which is termed an overflow chamber. Continuing with the description of the channel 16, it should be noted that extending upwardly from the overflow chamber 44 is a further channel segment 46 which extends beyond the upper edge 24 of the plastic sheet 22, and terminates in a closed end portion, this channel segment being termed a "vent" segment.

At this point, it should be noted that in FIG. 1 certain of the test channels 16 are illustrated including reagent discs in both test chambers 32 and 38, while others merely have reagent discs in the lower-most test chamber 32. This has been done solely for purposes of illustration, as the specific test to be performed with the tray 10, or the manner in which these tests are used to determine the identity of a microorganism are not critical to the present invention and disclosure which concerns the tray, per se. In this regard, a wide variety of known tests may be used and may require employment of reagent discs in both of the chambers 32 and 38 or merely in the chamber 32 or similarly only in the upper chamber 38. Therefore, for purposes of practicality and ease of manufacture, the test channels 16 have all been formed to a similar configuration.

With the above in mind, attention is now directed to FIGS. 4-6 for a more detailed discussion of the construction of the tray 10. In this regard, it should be noted that FIG. 5 is a conventional, transverse type sectional view taken through the channel 16 and the desiccant means 26 along the line 5—5 of FIG. 2. On the other hand, FIGS. 4 and 6 are sectional view of a less conventional nature, as FIG. 4 follows a section line which extends from the lower-most test chamber 32 through the upper test chamber 38 and the overflow chamber 44, with the cover being illustrated in the closed position and in section. FIG. 6, on the other hand, is a partial sectional view wherein the section line extends from the chamber 32 upwardly along the channel segment 30 and through the entering portion 18.

In FIG. 4, the cover 14 is shown in section, and a preferred method of pivotally attaching the cover member to the base 12 is illustrated. In this regard, the base 12 is provided at the upper edge thereof and at the remote corners of said edge, with flange portions 50 (also visible in FIG. 1), each including an aperture 52. The cover member 14 has a pair of oppositely disposed pin elements 54 formed on each end thereof, which pin elements 54 are disposed in the apertures 52 to effect pivotal mounting of the cover to the base 12. As an additional matter, it should be noted in FIG. 4, that the cover 14 is illustrated in the closed position, and includes a section of porous, absorbent material 56 on the undersurface thereof. With the cover 14 in the closed position, the absorbent section 56 overlies the base 12 and channel openings 18 for a purpose to be discussed more completely hereinafter.

The construction of the various segments of the testing channel 16 will now be considered in greater detail, looking first to the left-hand portion of FIG. 6 wherein the entry portion of the channel is illustrated. As can be seen from FIG. 6, and previously discussed FIGS. 1 and 2, the entry segment 18 is provided by a generally circular well defined by a wall section 60 from which extends the elongate channel segment 30. The first test chamber 32 is visible in the right-hand portion of FIG. 6 with the channel segment 30 opening into said chamber from the entry segment 18. The test chamber 32 is also of a circular configuration, with the wall surfaces thereof including a plurality of longitudinally extending ribs 62 which engage the periphery of the reagent disc 34 to maintain the disc in position above the floor or bottom 64 of the chamber 32. This spacing of the reagent disc 34 above the floor of the chamber 32 assures complete wetting of the reagent paper upon the introduction of the liquid specimen into the test chamber 32. Also visible in FIG. 6 is the section of clear plastic material 22 which overlies and closes the channel segment 30 and said test chamber 32, with the upper edge 24 disposed so as the entry segment 18 of the channel 16 remains uncovered.

The construction of the various chambers and channel sections which make up the other leg or portion of the test channel 16 can best be viewed with reference to FIG. 4, taken in conjunction with FIGS. 1 and 2 as previously discussed. In this regard, the first or lower test chamber 32 is illustrated to the right as viewed, and moving to the left from said chamber 32, there is illustrated a wall section 68 which serves to define partially the narrow channel section 36 (see FIG. 2), which channel section 36 interconnects the first test chamber 32 with the second test chamber 38. It should be noted that the second test chamber 38 is illustrated in section in both FIGS. 4 and 5 and includes a generally circular wall portion 70 upon which are formed two series of ribs 72 and 74. The first series of ribs 72 function similar to the previously discussed ribs 62 to engage the peripheral edge of the reagent disc 40 with the second series of ribs 74 extending inwardly to a greater extent to underlie and provide support for the disc 40 thereby maintaining the spacing above the bottom of the second test chamber 38 as illustrated. Extending from the second test chamber 38 at a level elevated with respect to the bottom or floor of said chamber, is the third narrow channel segment 42 which interconnects the second test chamber 38 with the overflow chamber 44. The channel segment 42 opens into the overflow chamber 44 and at a level disposed considerably above the bottom wall or floor of the overflow chamber 44, the vent channel 46 can be viewed as intersecting said overflow chamber and terminates beyond the edge 24 of the clear plastic sheet 22. Here again, the clear plastic sheet 22 overlies and closes the respective chambers 44, 38 and 32 as well as the various channel segments mentioned above.

Attention is now directed to the construction of the desiccant means 26, mentioned previously. In this regard, the base 12 includes, in addition to the various test channels 16, an elongate chamber 80, which is formed proximate one edge thereof, in the illustrated embodiment (see FIGS. 1, 2 and 5). Disposed in the chamber 80 is a desiccant element 82 of known construction, and capable of effectively purging or absorbing moisture from the air in said chamber or with which it is associated. Proximate the upper regions of the desiccant chamber 80, said chamber is in direct communication with an elongate dessicant channel 84 that extends along the length of the base 12 intersecting the entry segments 18 of each of the respective test channels 16, and terminating upon opening into the channel 16 furthest to the right as viewed in FIG. 1.

Accordingly, when the cover 14 is closed as shown in FIG. 4, said cover will overlie the desiccant channel section 84, the exposed end of the vent channel 46, and the entry portions 18 of the various test channels 16. Correspondingly, the sheet of clear plastic material 20 will overlie the testing segments 20 of the various channels 16. As such, there is in effect provided a closed system of interconnected channels, with the desiccant element 82 being in effective communication with each of the test chanels 16 via the elongate desiccant channel 84 and the entry portions 18 of each channel. As such, any air trapped in the various test channels 16 upon closing of the cover 14 and packaging of the tray will be effectively purged of moisture content by the desiccant element 82 thereby preventing the formation of undesirable condensate during storage, which condensate might adversely effect the result of the tests to be conducted with the tray 10.

Consideration is now directed to a preferred method of utilizing the tray 10, as illustrated in FIGS. 1-6 of the drawing and as discussed above. Initially, a urine or blood sample or the like is taken from a patient, and prepared in a conventional manner to produce a culture growth. Next, the tray 10 is opened and disposed in a vertical orientation, as shown in FIGS. 1 and 2, and a quantity of the prepared serum, designated generally 80, is injected into each of the testing channels 16. In this regard, it should be noted that prior to placement of the sheet 22 in position and packaging of the tray 10, the various reagent discs 34 and 40 are prepared in accordance with the desired tests that are to be performed. The reagent discs 34 and 40 are disposed in the test chambers 32 and 38, and the sheet 22 is secured in place. As such, there is provided a pre-prepared, disposable tray that can be used by the technician without extensive preparation and can be discarded once the tests are completed.

The quantity of liquid specimen injected into each test channel 16 is selected, so that with the tray in the vertical orientation of FIGS. 1 and 2, the specimen level 80 will fill the lower test chamber 32 and thereby saturate the reagent disc 34, as indicated. The tray 10 is then maintained in the vertical orientation for a prescribed period of time to allow the specimen to incubate fully and to react completely with the reagent disc in the first and lower test chamber 32. Subsequently, after expiration of the abovementioned period of time, the tray 10 is tipped or rotated 90° to an orientation as illustrated in FIG. 3. This repositioning of the tray 10 will cause the liquid specimen 80 to enter the second test chamber 38, and saturate the second reagent disc 40 disposed therein. At this point, it is contemplated that the specimen would have fully reacted with the various reagent discs to produce the desired positive or negative test indications, with respect to the individual tests being performed. However, if additional time is required, the tray may be maintained in the tipped or rotated orientation of FIG. 3 without problem or concern to the microbiologist or technician. Once the tests are completed, the microbiologist can compare the results of the various tests with known test patterns for specific microorganisms, and thereby obtain an identification as to the microorganism present in the specimen.

During the initial positioning of the tray 10 or the tipping stages any gases which may develop in the test channel 16, may escape via the vent channel 46, as the distal end of this channel extends beyond the plastic sheet 22 and is open to the atmosphere. As a further matter, should the quantity of liquid 81 introduced in the test channel 16 be in excess of that as desired, the overflow chamber 44 serves to accommodate any excess, upon the tipping of the tray from the position as illustrated in FIG. 2, to that of FIG. 3, assuring that undesired spillage of the specimen will not occur, which spillage could contaminate adjacent tests as well as subject the technician to infection by the microorganism present.

As a further matter, as was alluded previously, during injection of the specimen into the individual test channels 16, it is possible that small quantities of the specimen may be spilled or remain on the upper surface portions of the tray 10, giving rise to a danger that the technician may be infected. The cover member 14 serves to protect the technician against contamination by the microorganism that when closed the porous layer 56 will absorb any excess specimen.

A preferred embodiment of the present invention has been illustrated and described above. While the specific structural features discussed constitute preferred forms, they are not intended to limit the invention, as it is contemplated that those skilled in the art and possessed with the form of the invention illustrated may devise alternate structures without departing from the spirit and scope of the invention, as defined in the claims appended hereto.

The invention is claimed as follows:

1. A testing tray comprised of a plurality of testing channels for the conducting of a plurality of identification tests, or the like, in conjunction with a liquid specimen, said tray being capable of use with the testing channels in a generally vertical orientation comprising: a base having a plurality of separate testing channels formed therein, each said channel being of a reverse bend configuration and including at a first end thereof an entry portion for the introduction of a liquid specimen, and a vent segment at the opposite end, with a testing portion intermediate said channel ends, transparent sheet means affixed to and overlying said base to cover the testing portion of each said channel and effective to isolate each testing channel from the other while leaving the entry portion and the vent segment of each testing channel substantially open, a cover member pivotally mounted to said base adjacent said entry portion and the vent segment of the respective channels, said cover member being movable between a first, open position, wherein access to said entry portion is provided and said vent segment is open, and a second, closed position, wherein said cover overlies both said entry portion and said vent segment said cover member including a section of porous absorbent material engaged against said base and overlying those portions of the entry portions and the vent segments of the respective channels which are not covered by the transparent sheet means when said cover member is in the closed position, with said porous, absorbent material adapted to absorb any excess liquid specimen at either the entry portion or the vent segment of the testing channels, and due to the porous nature of said material, enabling said vent segment ot function even though the cover member is in the second, closed position, and said base including a desiccant chamber formed therein, with channel means interconnecting each said testing channel with said desiccant chamber, such that a dessicant element may be placed therein to extract undesired moisture from each said testing channels prior to use of the tray.

2. A testing tray for the conducting of a plurality of identification tests or the like in conjunction with a liquid specimen, said tray comprising, a base having a plurality of separate testing channels formed therein, each said channel including an entry port for the introduction of a liquid sample and a testing portion, transparent means affixed to said base member and overlying the testing portion of each channel, while leaving the entry portion of the respective channels open, and cover means adapted to overlie the entry portion of said channel, the improvement, wherein said base includes a desiccant chamber formed therein, with a desiccant element disposed in said chamber, with said transparent means overlying said desiccant element and said desiccant chamber, and channel means formed in said base and interconnecting each of said testing channels with each said desiccant chamber such that when said cover is in the closed condition, said desiccant element will extract undesired moisture from each said testing chambers, prior to or during use of said tray.

3. A testing tray according to claim 2, wherein said cover means includes a cover member pivotally mounted to said base adjacent said entry portion of the respective channels, said cover member being movable between a first, open position, and a second, closed position in overlying relation to said entry portion of each channel, said cover member including a section of absorbent material engaged against said base and overlying said entry portion of the respective channels when said cover member is in the closed position.

4. A testing tray according to claim 2, wherein each said testing channel includes wall structure defining at least one reagent chamber adapted to accept a reagent disc, said wall surface including a plurality of longitudinally extending ribs for engagement with the periphery of the reagent discs disposed therein, so as to maintain said disc in said proper position.

5. A testing tray according to claim 2, wherein each said testing channel includes an entry port defined by a generally circular well, with an elongate, narrow first channel section extending therefrom and terminating in a first test chamber adapted to receive a reagent disc, a second channel segment extending upwardly from said first test chamber and spaced from and parallel to said first channel section, said second channel section opening into a second test chamber adapted to receive a reagent disc, and an overflow chamber disposed above said second test chamber and connected thereto by channel means, said overflow chamber including a channel segment which is open to the atmosphere.

6. A testing tray according to claim 5, wherein said testing channel includes wall surfaces having rib means formed thereon for engaging the periphery of a reagent disc, and for providing underlying support to said reagent disc, whereby the disc can be maintained in proper position in spaced relation to the bottom surface of said test chamber.

* * * * *